United States Patent
Cramer et al.

(10) Patent No.: US 10,394,135 B2
(45) Date of Patent: Aug. 27, 2019

(54) METHOD AND APPARATUS FOR MEASURING A PARAMETER OF A LITHOGRAPHIC PROCESS, COMPUTER PROGRAM PRODUCTS FOR IMPLEMENTING SUCH METHODS AND APPARATUS

(71) Applicant: ASML Netherlands B.V., Veldhoven (NL)

(72) Inventors: Hugo Augustinus Joseph Cramer, Eindhoven (NL); Bastiaan Onne Fagginger Auer, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/796,298

(22) Filed: Oct. 27, 2017

(65) Prior Publication Data
US 2018/0129140 A1 May 10, 2018

(30) Foreign Application Priority Data

Nov. 4, 2016 (EP) .................................... 16197204

(51) Int. Cl.
*G03F 7/20* (2006.01)
*G01N 21/47* (2006.01)

(52) U.S. Cl.
CPC ......... *G03F 7/70625* (2013.01); *G01N 21/47* (2013.01); *G03F 7/705* (2013.01); *G03F 7/7085* (2013.01); *G03F 7/70616* (2013.01)

(58) Field of Classification Search
None
See application file for complete search history.

(56) References Cited

U.S. PATENT DOCUMENTS

| | | |
|---|---|---|
| 7,522,293 B2 | 4/2009 | Wu et al. |
| 2005/0197772 A1 | 9/2005 | Archie et al. |
| 2006/0066855 A1 | 3/2006 | Boef et al. |

(Continued)

FOREIGN PATENT DOCUMENTS

| | | |
|---|---|---|
| WO | WO 2015/082158 A1 | 6/2015 |
| WO | WO 2015/090721 A1 | 6/2015 |
| WO | WO 2017/032736 A1 | 3/2017 |

OTHER PUBLICATIONS

Von Clarmann et al, "On the role of non-random errors in inverse problems in radiative transfer and other applications," *Journal of Quantitative Spectroscopy & Radiative Transfer*, vol. 71, Oct. 1, 2001, Amsterdam, Netherlands; pp. 39-46.

(Continued)

*Primary Examiner* — Michelle M Iacoletti
(74) *Attorney, Agent, or Firm* — Sterne, Kessler, Goldstein & Fox P.L.L.C.

(57) ABSTRACT

Disclosed is a method of measuring a parameter of interest relating to a structure on a substrate, and associated metrology apparatus. The method comprises determining a correction to compensate for the effect of a measurement condition on a measurement signal from a plurality of measurement signals, wherein each of said measurement signals results from a different measurement of the structure performed under a different variation of said measurement condition. The correction is then used in a reconstruction of a mathematical model of said structure to suppress an influence of variations of said measurement condition on the reconstruction.

17 Claims, 3 Drawing Sheets

(56) References Cited

U.S. PATENT DOCUMENTS

2012/0123748 A1 5/2012 Aben et al.
2014/0354969 A1 12/2014 Elings et al.
2015/0177166 A1 6/2015 Cramer et al.
2015/0316490 A1 11/2015 Amit et al.
2016/0313653 A1 10/2016 Mink et al.

OTHER PUBLICATIONS

Qin et al., "Deep subwavelength nanometric image reconstruction using Fourier domain optical normalization," *Light: Science and Applications*, vol. 5, Feb. 26, 2016, New York, NY; pp. 1-9.

International Search Report and Written Opinion of the International Search Authority directed to related International Patent Application No. PCT/EP2017/076991, dated Jan. 16, 2018; 12 pages.

Schäfer et al., "A Shrinkage Approach to Large-Scale Covariance Matrix Estimation and Implications for Functional Genomics," *Statistical Applications in Genetics and Molecular Biology*, vol. 4, No. 1, Jan. 2005, Berlin, Germany; pp. 1-30.

METHOD AND APPARATUS FOR MEASURING A PARAMETER OF A LITHOGRAPHIC PROCESS, COMPUTER PROGRAM PRODUCTS FOR IMPLEMENTING SUCH METHODS AND APPARATUS

BACKGROUND

Field of the Invention

The present invention relates to methods and apparatus for measuring a structure on a substrate and models for error correction. The invention may be applied for example in model based metrology of microscopic structures, for example to assess critical dimensions (CD) or overlay performance of a lithographic apparatus.

Background

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth (CD) of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. Two main types of scatterometer are known. Spectroscopic scatterometers direct a broadband radiation beam onto the substrate and measure the spectrum (intensity as a function of wavelength) of the radiation scattered into a particular narrow angular range. Angularly resolved scatterometers use a monochromatic radiation beam and measure the intensity of the scattered radiation as a function of angle.

By comparing the properties of the beam before and after it has been reflected or scattered by the substrate, the properties of the substrate can be determined. This can be done, for example, by comparing data obtained from measurement of the reflected or scattered beam with model (simulated) diffraction signals calculated from a parameterized model. The calculated signals can be pre-calculated and stored in a library, the library representing a plurality of candidate substrate structures distributed in a parameter space of the parameterized model. Alternatively or in addition, parameters can be varied during an iterative search process, until a calculated diffraction signal matches the measured signal. In U.S. Pat. No. 7,522,293 (Wu) and US 2012/0123748A1, for example, these two techniques are described for example as 'library based' and 'regression based' processes, respectively.

In particular for complex structures, or structures including particular materials, the number of parameters required to model the scattered beam accurately is high. A 'model recipe' is defined in which parameters are defined as either given ('fixed') or variable ('floating'). For floating parameters, the permitted range of variation is defined, either in absolute terms or by reference to deviation from a nominal value. Each floating parameter in the model represents another 'degree of freedom' in the model, and consequently another dimension in the multidimensional parameter space in which the best matching candidate structure is to be found. Even with a handful of parameters, the size of computational tasks quickly becomes very large, for example by raising the number of library samples unacceptably. It also raises the risk of falsely matching parameter sets that do not correspond to the measured substrate. Fixing a parameter to a value that is not identical to what is actually in the measured structure in some cases may have little impact on the reconstruction. Other times, however, differences between the fixed value and the real value of the parameter may distort the matching process significantly so that inaccuracy arises in reconstruction of the parameters of interest.

Such fixed parameters make it difficult to find the right compromise between accuracy and practicality of computation. Fixed parameters may be parameters of the model of the structure being measured, but they may also be parameters of an apparatus used to obtain measurements, or another aspect of the measurement. That is to say, a varied measurement condition, such as measurement using different apparatuses, may obtain slightly different diffraction signals from the same structure, and therefore yield slightly different measurements of a parameter of interest.

It would be desirable to mitigate for the effects of different variations of a measurement condition.

SUMMARY OF THE INVENTION

In a first aspect of the invention, there is provided a method of measuring a parameter of interest relating to a structure on a substrate, comprising: 1) determining a correction to compensate for the effect of a measurement condition on a measurement signal from a plurality of measurement signals, wherein each of said measurement signals results from a different measurement of the structure performed under a different variation of said measurement condition; and 2) performing a reconstruction of a mathematical model of said structure using the correction to suppress an influence of variations of said measurement condition on the reconstruction.

In a second aspect of the invention, there is provided a metrology apparatus, comprising: a support for a substrate on which a structure is formed; an optical system for selectively illuminating said structure with radiation and collecting at scattered radiation which has been scattered by the structure, for a plurality of different variations of a measurement condition; a detector for detecting a measurement signal from the scattered radiation, for each variation of a measurement condition; and a processor arranged to determine a correction to compensate for the effect of the measurement condition on a measurement signal from the measurement signals detected.

The invention also provides a computer program product comprising machine readable instructions which, when run on a suitable processor, cause the processor to perform the method of the first aspect.

The invention also provides a lithographic system comprising: a lithographic apparatus for use in a lithographic process; and a metrology apparatus according to the second aspect.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example, with reference to the accompanying drawings in which.

DETAILED DESCRIPTION

Before describing embodiments of the invention in detail, it is instructive to present an example environment in which embodiments of the present invention may be implemented.

Figure 1:
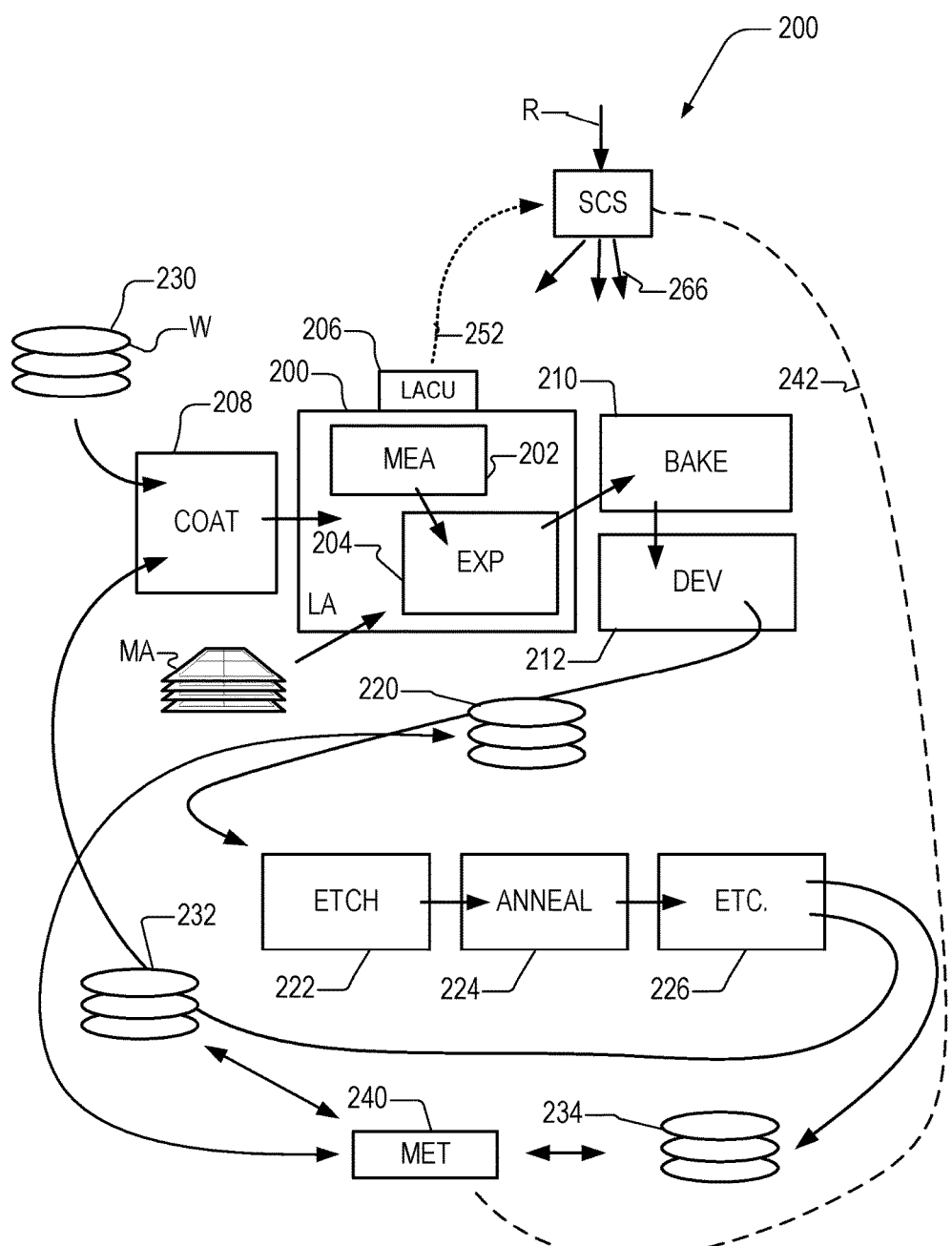
FIG. 1 depicts a lithographic apparatus together with other apparatuses forming a production facility for semiconductor devices.

FIG. 1 at 200 shows a lithographic apparatus LA as part of an industrial production facility implementing a high-volume, lithographic manufacturing process. In the present example, the manufacturing process is adapted for the manufacture of for semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a sub-system or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example is of a so-called dual stage type which has two substrate tables and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses. As another example, apparatus and processing steps may be provided for the implementation of self-aligned multiple patterning, to produce multiple smaller features based on a precursor pattern laid down by the lithographic apparatus.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system which receives some or all of the substrates W that have been processed in the litho cell. Metrology results are provided directly or indirectly to the supervisory control system SCS. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 240 which is provided for making measurements of parameters of the products at desired stages in the manufacturing process. A common example of a metrology station in a modern lithographic production facility is a scatterometer, for example an angle-resolved scatterometer or a spectroscopic scatterometer, and it may be applied to measure properties of the developed substrates at 220 prior to etching in the apparatus 222. Using metrology apparatus 240, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. The metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work.

Additionally, metrology apparatus 240 and/or other metrology apparatuses (not shown) can be applied to measure properties of the processed substrates 232, 234, and incoming substrates 230. The metrology apparatus can be used on the processed substrate to determine important parameters such as overlay or CD. In accordance with embodiments of the present disclosure, the metrology apparatus is used to measure properties of structures having the same material and dimensions as functional product structures, which have been formed using one or more lithographic steps, etching and other processes after lithographic exposure.

Figure 2:
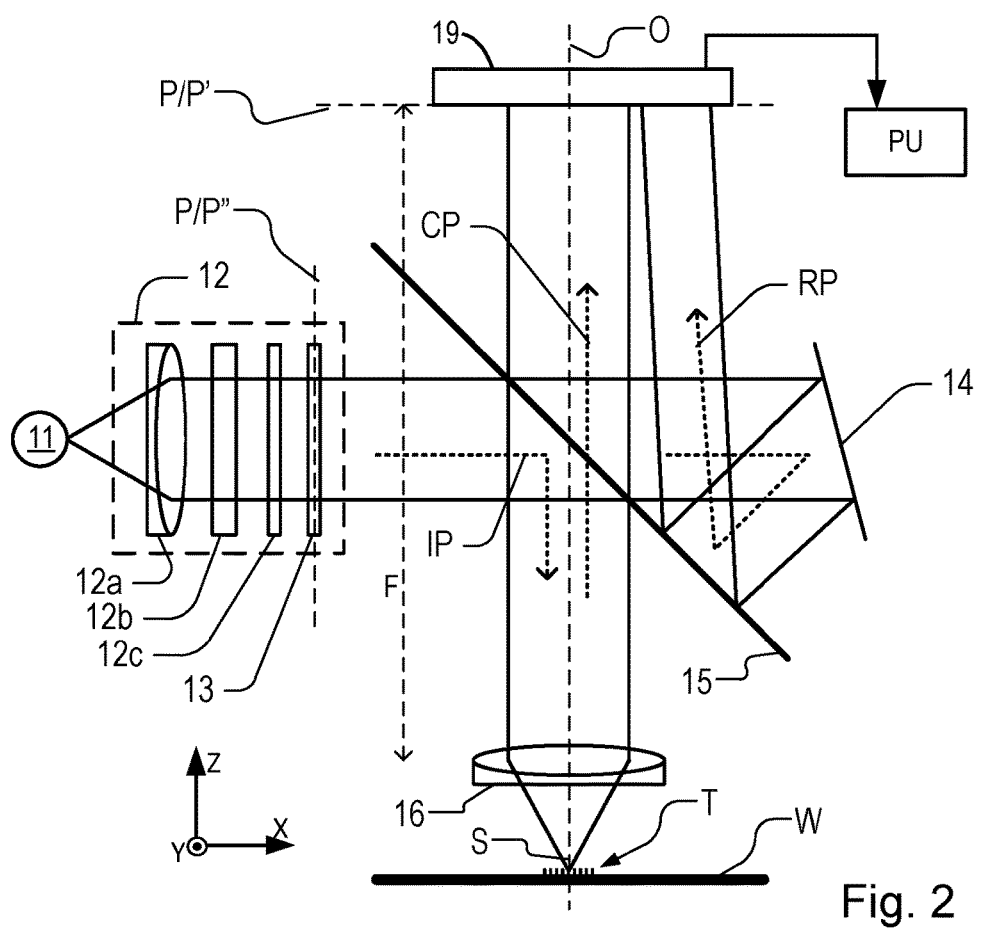
FIG. 2 depicts a scatterometer configured to capture an angle-resolved scatter spectrum according to an embodiment of the present invention.

FIG. 2 shows the basic elements of a known angle-resolved scatterometer that may be used as a metrology apparatus in embodiments of the present disclosure. In this type of metrology apparatus, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), for example at least 0.9 or at least 0.95. Immersion fluid can be used to obtain with numerical apertures greater than 1, if desired.

As in the lithographic apparatus LA, one or more substrate tables may be provided to hold the substrate W during measurement. Coarse and fine positioners may be configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and/or Y directions to acquire different targets, and in the Z direction to obtain a desired focusing of the optical system on the target. It is convenient to think and describe operations as if the objective lens and optical system being brought to different locations on the substrate, when in practice the optical system may remain substantially stationary and only the substrate moves. In other apparatuses, relative movement in one direction is implemented by physical movement of the substrate, while relative movement in orthogonal direction is implemented by physical movement of the optical system. Provided the relative position of the substrate and the optical system is correct, it does not matter in principle whether one or both of those is moving in the real world.

When the radiation beam is incident on the beam splitter 16 part of it is transmitted through the beam splitter (partially reflecting surface 15) and follows a reference path RP towards a reference mirror 14.

Radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and may instead be re-imaged with auxiliary optics (not shown) onto the detector located in a so-called conjugate pupil plane P'. The detector may be a two-dimensional detector so that a two-dimensional angular scatter spectrum or diffraction spectrum of a substrate target 30 can be measured. In the pupil plane or conjugate pupil plane, the radial position of radiation defines the angle of incidence/departure of the radiation in the plane of focused spot S, and the angular position around an optical axis O defines azimuth angle of the radiation. The detector 19 may be, for example, an array of CCD or CMOS sensors, and may use an integration time of, for example, 40 milliseconds per frame.

Radiation in reference path RP is projected onto a different part of the same detector 19 or alternatively on to a different detector (not shown). A reference beam is often used for example to measure the intensity of the incident radiation, to allow normalization of the intensity values measured in the scatter spectrum.

The various components of illumination system 12 can be adjustable to implement different metrology 'recipes' within the same apparatus. Color filter 12b may be implemented for example by a set of interference filters to select different wavelengths of interest in the range of, say, 405-790 nm or even lower, such as 200-300 nm. An interference filter may be tunable rather than comprising a set of different filters. A grating could be used instead of interference filters. Polarizer 12c may be rotatable or swappable so as to implement different polarization states in the radiation spot S. Aperture device 13 can be adjusted to implement different illumination profiles. Aperture device 13 is located in a plane P''' conjugate with pupil plane P of objective lens 16 and the plane of the detector 19. In this way, an illumination profile defined by the aperture device defines the angular distribution of light incident on substrate radiation passing through different locations on aperture device 13.

The detector 19 may measure the intensity of scattered light at a single wavelength (or narrow wavelength range), or it may measure the intensity separately at multiple wavelengths, or integrated over a wavelength range. Furthermore, the detector may separately measure the intensity of transverse magnetic- and transverse electric-polarized light and/or the phase difference between the transverse magnetic-polarized light and transverse electric-polarized light.

In the known angle-resolved scatterometer represented schematically in FIG. 2, a metrology target T is provided on substrate W. For measurements, this target may comprise a 1-D grating, which is printed such that after development, it is an array of solid resist lines. Alternatively, the target may be a 2-D grating, which is printed such that after development, the grating is formed of solid resist pillars or vias (contact holes) in the resist. The bars, pillars or vias may alternatively be etched into the substrate. Measurements of parameters such as line widths and shapes, may be obtained by an iterative reconstruction process, performed by processing unit PU, from knowledge of the printing step and/or other scatterometry processes. Targets may also contain more complex structures such as parts of a DRAM product cell.

In addition to measurement of parameters by reconstruction, angle-resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement using the instrument of FIG. 2 are described for example in published patent application US2006066855A1 cited above. Simply stated, while the positions of the higher diffraction orders (1st order and above) in the diffraction spectrum of a periodic target are determined only by the periodicity of the target, asymmetry of intensity levels in the diffraction spectrum is indicative of asymmetry in the individual features which make up the target. In the instrument of FIG. 2, where detector 19 may be an image sensor, such asymmetry in the higher diffraction orders appears directly as asymmetry in the pupil image recorded by detector 19. This asymmetry can be measured by digital image processing in unit PU, and calibrated against known values of overlay.

A detailed description of pattern reconstruction processes such as 'regression based' and 'library based' methods, as well as a description of different types of scatterometers, can be found in US 2012/0123748A1. The present document describes the use of a method for avoiding and/or correcting errors in a 'regression based' reconstruction process. Such a method may be used in other reconstruction models such as 'library based' processes, hybrids of regression and library processes, and to direct inversion based processes. The proposed method can be applied in different reconstruction processes.

CD or profile reconstruction (for example) using scatterometry tries to resolve parameters of interest (e.g. CD, side-wall angle, layer thickness, refractive index), from reflectivity measurement of a structure on a substrate. The structure may comprise either special designed targets in scribelanes or dummy areas, or directly on repeating structures in the device area.

From the reflectivity measurement data, the structure or profile giving rise to the detected spectrum (or "pupil") may be reconstructed by calculation within processing unit PU. The reconstruction can be performed for example by Rigorous Coupled Wave Analysis and non-linear regression. In general, for the reconstruction the general form of the structure is known and some parameters are assumed from knowledge of the process by which the structure was made, leaving only a few parameters of the structure to be determined from the scatterometry data. Simply stated, the reconstruction process may comprise simulating the spectrum or pupil response of a modelled structure and comparing this to the actual measured spectrum. Assuming that the simulated and measured spectra are not a perfect match, the values of one or more parameters of the model will be altered and the spectrum response re-simulated. This is repeated until the mismatch between the simulated and measured spectra is minimized.

CD or profile reconstruction requires that the nominal stack geometry and optical material are well known and relies on the fact that small deviations from nominal can be reconstructed in the fitting process. In this process, measurement data are fitted by the simulations which are based on numerically solving the reflection equations of electromagnetic waves (Maxwell equations) as a function of parameter deviations, combined with (known/modelled) properties of the measurement sensor.

The modelled parameter values (e.g., geometry and/or optical material parameters) which result in the closest match between the simulated spectrum and the measured spectrum is considered to contain the actual values of the parameters of interest (e.g., CD, SWA). However, some parameters in the model are fixed (e.g., optical material parameters) and other parameters are not part of the model at all, but will affect the measurement and therefore the diffraction pattern. These may include, for example, target position (with respect to the measurement spot) in X and/or Y (where X and Y are in the plane of the target as indicated in FIG. 2), measurement focus (e.g., target position in Z as indicated in FIG. 2), the sensor used and the measurement radiation wavelength/bandwidth.

When comparing the simulated spectrum and the measured spectrum, it is assumed that the residual intensities (difference between the measured and modeled intensities) have a normal distribution with zero mean and a variance given by a (e.g., diagonal) covariance matrix $C_I$ which models the detector (e.g. detector 19) CCD dark current and shot noise. This ensures that pixels that have a poor signal-to-noise ratio (SNR) with respect to the detector noise are underweighted with respect to pixels that have a good SNR.

There is a trend towards measuring increasingly smaller targets (from 40 µm square to 4.5 µm square via intervening dimensions). This causes an increasing contribution of nuisance signals from the environment to the measured pupil, which is not simulated by the forward model used for reconstruction and can therefore interfere with the measurement of the parameter of interest (e.g., CD). In particular, the impact of positioning errors on parameters of interest becomes more significant for smaller targets.

It is therefore proposed to perform a reconstruction based measurement wherein repeated measurements are made of the target during which a measurement condition is varied (e.g., a measurement parameter such as those mentioned above is changed deliberately or part of the measurement sequence is repeated), while the parameter(s) of interest is/are maintained constant (e.g., the repeated measurements are of the same physical target structure). The measurement parameter will be a parameter against which robustness is desired (i.e., the effect of which is to be minimized). Such a method is applicable to any measurement tool that uses reconstruction methods where a residual (for example a residual intensity for each illumination angle, or a residual ellipsometer signal for each wavelength) between a measured and modeled signal is minimized. Using the multiple measurements of a target, a correction can be determined which can be used in the minimization to mitigate the effect of the measurement condition.

In an embodiment, the correction may comprise a weighting function or weighting matrix (e.g., a covariance matrix) which imposes weights on each component (e.g., pixel) in the residual. This weighting matrix may be additional to weighting imposed with respect to the detector noise model by e.g., using a covariance matrix $C_I$. In such an embodiment, the covariance matrix $C_I$ may be replaced by a new covariance matrix C, such that:

$$C = C_I + C_r \qquad \text{Equation (1)}$$

where weighting matrix $C_r$ is determined from the multiple measurements per target under varying measurement conditions. In another embodiment, the weighting matrix $C_r$ will be used as a correction by itself, without covariance matrix $C_I$.

The measurement condition or parameter against which robustness is desired may comprise one or more of the following, for example:

1. Position in X and/or Y (for wafer alignment robustness)—each of the multiple measurements of a target may be performed with a different displacement of the measurement spot with respect to the target center (or other point); for example an XY-matrix scan over a single target.

2. Focus (for focus robustness)—each of the multiple measurements of a target may be performed at a different focus level; for example a Z-scan over a single target (wherein the target is measured at multiple height levels).

3. Detector/Metrology apparatus (for tool matching robustness)—each of the multiple measurements of a target may be performed using a different sensor and/or metrology apparatus.

4. Substrate unloading and reloading (for dynamic repro robustness)—measurements of a target may be performed on the same target before and after a substrate unloading and reloading operation, i.e., when the same substrate is unloaded from the metrology apparatus and then reloaded.

5. A measurement radiation parameter (for measurement radiation robustness)—each of the multiple measurements of a target may be performed on the same target with one or more parameters of the measurement radiation varied, e.g., wavelength, wavelength band, beam angle of incidence and/or bandwidth.

In an embodiment, it is proposed to combine such data from multiple measurement conditions, e.g., by adding two or more weighting matrices, each weighting matrix obtained for multiple measurements of the same target, but with a different measurement condition varied (care should be taken to combine independent variations in this case). For example, an alignment position (X/Y) weighting matrix obtained from multiple measurements of a target at different positions in X/Y may be added to a focus (Z-position) weighting matrix obtained from multiple measurements of the same target at different positions in Z (and possibly to one or more other weighting matrices, each corresponding to another varied measurement condition.

Another embodiment may comprise averaging different covariance matrices (each corresponding to variation of the same measurement parameter) from measurements of multiple targets, since the parameter of interest variations can couple to the measurement condition variations. The multiple targets may all be similar; i.e., of the same application (same design/pattern). In such an embodiment, measurement of a first target may be performed under multiple measurement conditions relating to variation of a measurement parameter (e.g., different alignments) and measurement of a second (similar) target may be performed under multiple measurement conditions, relating to variation of the same measurement parameter (e.g., different alignments). The resultant matrices from the first and second targets may then be averaged.

The embodiments of the two preceding paragraphs may be combined, such that an averaged weighting matrix obtained from multiple targets with a first measurement parameter varied may be added to an averaged weighting matrix obtained from (e.g., the same) multiple targets with a second measurement parameter varied.

There are a number of ways of calculating the weighting matrix $C_r$. Considering an example where $I_1, \ldots, I_N$ are the measurement signals (e.g., vectors of measured pupil intensities or measurement spectra) of the same target from N measurements (over which a measurement condition is varied), a first method may comprise giving a lesser weighting to components (e.g., pixels) during reconstruction which vary more over the N measurements, e.g., those pixels which show the greatest dependence on the measurement parameter. In this way, these pixels will have a smaller impact on the reconstructed profile parameters. In a more specific embodiment, the weighting matrix may be a diagonal (variance) matrix describing the variance of the ith pixel across all N measurements:

$$(C_r)_{ii} = \mathrm{var}((I_1)_i, \ldots, (I_N)_i) \qquad \text{Equation (2)}$$

The example of Equation (2) does not capture any dependencies between different pixels, which may be significant. Therefore, in another embodiment, an entire covariance matrix $C_r$ is calculated:

$$C_r = \frac{1}{N-1} \sum_{j=1}^{N} (I_j - I_{avg})(I_j - I_{avg})^T \qquad \text{Equation (3)}$$

where $I_{avg}$ is the average intensity over the N measurements and may be defined as:

$$I_{avg} = \frac{1}{N} \sum_{j=1}^{N} I_j$$

Such a covariance matrix suppresses the coupling of the different pixels due to the measurement condition variations, and therefore suppressing both individual variances of each pixel and common variations between different pairs of pixels.

Not all variations found in the measured pupils are equally likely to occur. For example, very large positional errors are less likely to occur than small positional errors. Therefore, in a variation on the example of Equation (3), the different measurements can be weighted by a weighting factor $p_j$ (where $p_j \in [0,1]$ and $\Sigma_{j=1}^{N} p_j = 1$) reflecting the likelihood that the measurement parameter has the specific value corresponding to the measurement. Where, for example, the measurement parameter comprises position, values for the weighting factor $p_j$ (for the different positional errors) may (for example) be obtained from sensor population data for positioning accuracy. In this embodiment $C_r$ may be calculated by:

$$C_r = \frac{N}{N-1} \sum_{j=1}^{N} (I_j - I_{avg}) p_j (I_j - I_{avg})^T \qquad \text{Equation (4)}$$

In other embodiments, a more advanced and stable estimation of the covariance matrix may be obtained by using a suitable estimator, in particular for cases where the number of measurements N is smaller than the number of measured intensities, i.e. the dimensionality of the vectors $I_j$. The estimator may, for example, comprise one of:

- a shrinkage covariance estimator, where a convex linear combination of Equation (4) and another matrix is taken, wherein the other matrix may be, for example, one of those listed in Table 2 of "A Shrinkage Approach to Large-Scale Covariance Matrix Estimation and Implications for Functional Genomics", Schäfer and Strimmer, Statistical Applications in Genetics and Molecular Biology Volume 4, Issue 1, Article 32, which can be found at http://strimmerlab.org/publications/journals/shrinkcov2005.pdf and is hereby incorporated by reference in its entirety;
- a banding estimator where the matrix described by Equation (4) has all entries outside of a suitably chosen band around its diagonal set to 0; or
- a tapering estimator where the matrix described by Equation (4) has its entries $(C_r)_{ij}$ decay by a function of the matrix entry's distance to the matrix diagonal $t(|i-j|)$; e.g., a piecewise linear tapering function which linearly decays from 1 to 0 as the distance to the diagonal increases.

The covariance matrix may be measured per application (i.e., per different structure/design/pattern). It can be seen that there is an application dependent coupling between the parameters of interest and measurement parameters inside the pupil; a different structure can couple differently to the variations in illumination and detection to, for example, a positioning error.

In practice the covariance matrix (correction) may be determined in a calibration step. The calibration step may comprise a measurement of a target under, say, XY-displacements (or other parameter variation), measuring the associated signals (angle-dependent intensities) and then determining a covariance matrix from the variations of these intensities under the XY-displacements. Applying the correction would then comprise applying the inverse of the determined covariance matrix to the difference between the measured intensities and modeled intensities "on the fly" during measurements at a later stage.

Figure 3:
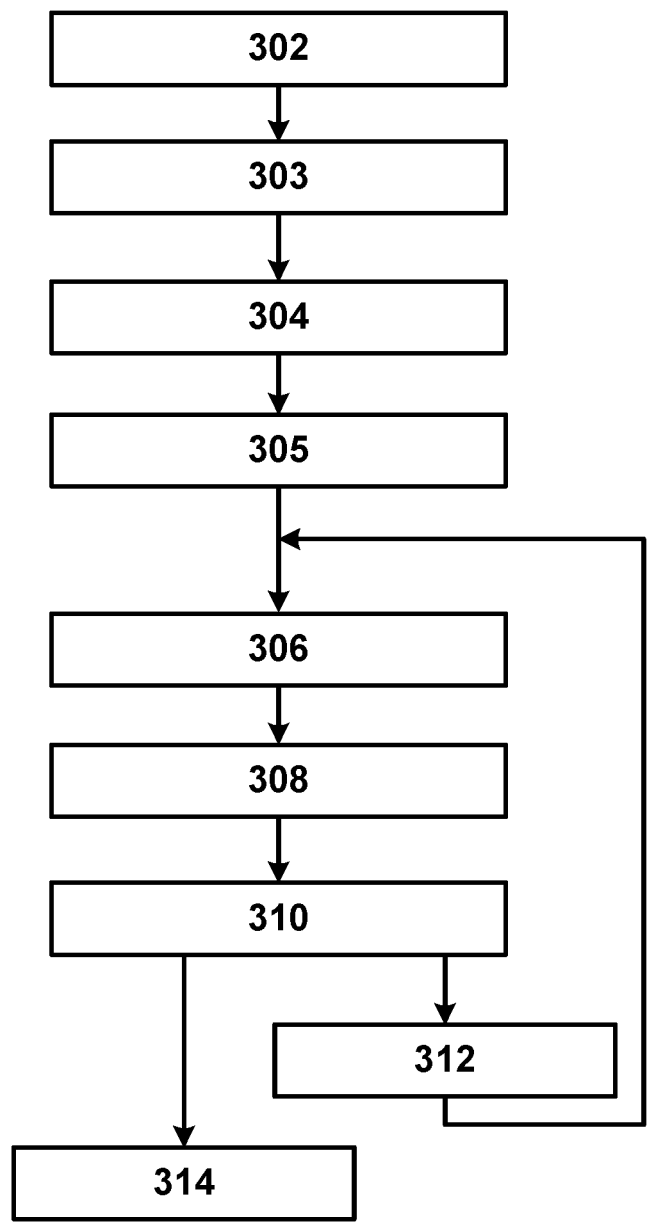
FIG. 3 is a flowchart describing a method according to an embodiment of the invention.

FIG. 3 illustrates a 'regression based' process for reconstruction of a target using a parameterized model and diffraction patterns (diffraction spectra or pupil) detected using an inspection apparatus such as a scatterometer. In this type of reconstruction process, a diffraction pattern based on a first estimate of the target shape (a first candidate structure) is calculated and compared with the measured diffraction pattern. The calculation simulates the interaction between radiation and the structure described by the model. Parameters of the model are then varied systematically and the diffraction pattern re-calculated in a series of iterations, to generate new candidate structures and so arrive at a best fit. The target will be assumed for this description to be a structure periodic in one direction, as described with reference to FIG. 3, for example. In practice it may be periodic in two (or more) directions, and the processing will be adapted accordingly. The diffraction pattern may be for example a 2-D pupil image detected by sensor 19 in the scatterometer of FIG. 2.

In the terminology of the introduction and claims, the diffraction pattern measured by the scatterometer is an example of a detected signal. The diffraction patterns calculated using the parameterized model are examples of model signals. The steps of the method in more detail are as follows:

302: A 'reconstruction model' is established which defines a parameterized model of the target structure in terms of a number of parameters Pi (P1, P2, P3 and so on). These parameters may represent for example, in a 1-D periodic structure, the angle of a side wall, the height or depth of a feature, the width of the feature. Material properties of the target and underlying layers are also represented by parameters such as refractive index (at a particular wavelength present in the scatterometry radiation beam). Importantly, while a target structure may be defined by dozens of parameters describing its shape and material properties, the reconstruction model will define many of these to have fixed values, while others are to be variable or 'floating' parameters for the purpose of the following process steps. In the prior publication US 2012/0123748A1 a process is described by which the choice between fixed and floating parameters is made. The set of choices can be referred to as a 'recipe' for the reconstruction process, and different recipes can be tried. For example, the prior publication introduces ways in which parameters can be permitted to vary without being fully independent floating parameters. These techniques can be adopted or not, in implementing the present invention. For the purposes of describing FIG. 3, only the floating parameters are considered as parameters Pi.

303: A model target shape is estimated by setting initial values Pi(0) for the floating parameters (i.e. P1(0), P2(0), P3(0) and so on). Each floating parameter will be generated within certain predetermined ranges, as defined in the recipe.

304: Using for example a scatterometer, the diffraction pattern of the actual target on the substrate is measured a number of times, each of these measurements being performed with a different variation of a measurement condition (e.g., a measurement parameter) related to the measurement (rather than the target), such that all parameters Pi remain unchanged. The measured diffraction patterns are forwarded to a calculation system such as a computer. In particular the measurement parameter may be target position relative to the measurement spot (in which case the different measurements will be of the same target at different positions in X and/or Y), focus (in which case the different measurements will be of the same target at different focus levels or positions in Z), reproducibility (in which case the different measurements will be of the same target before and after unloading and loading operations), detector apparatus (in which case the different measurements will be of the same target measured using a different detector or metrology apparatus) or a measurement radiation parameter such as wavelength or bandwidth (in which case the different measurements will be of the same target performed with different wavelength or bandwidth measurement radiation). The calculation system may be the processing unit PU referred to above, or it may be a separate apparatus.

305: A correction is calculated which mitigates the effect of the measurement parameter varied across the measurements performed in step 304. The correction may comprise a weighting matrix $C_r$, such as a variance/covariance matrix describing the variance across the detected pixel intensities for each pixel. The variance/covariance matrix may be calculated according to any of Equations (2), (3) or (4). The variance/covariance matrix may also include any variation described herein; e.g., an estimator may be used, or the weighting matrix may be the sum of different weighting matrices obtained with different measurement conditions varied, and/or may be averaged over different targets. The correction may comprise covariance matrix C of Equation (1), which also includes weighting based on the detector model.

306: The parameters representing the estimated shape of the target, together with material properties of the different elements of the modeled target, are used to calculate the scattering behavior. This may be done for example using a rigorous optical diffraction method such as RCWA or any other solver of Maxwell's equations. This gives the model diffraction pattern for the estimated target shape.

308, 310: The measured diffraction pattern and the model diffraction pattern are then compared and their similarities and differences are used to calculate a "merit function" for the model target shape. In the novel method disclosed herein, the correction calculated at step 305 is used in the calculation of the merit function to reduce the influence of the variation of the measurement condition. In this manner, the correction is applied at every iteration of the minimization of the merit function. For example, the correction may be applied to a calculated residual between measured diffraction pattern and the model diffraction pattern at each iteration, the residual being used in the merit function.

312: Assuming that the merit function indicates that the model needs to be improved before it represents accurately the actual target shape, new parameters P1(1), P2(1), P3(1), etc. are estimated and fed back iteratively into step 306. Steps 306-312 are repeated, so as to search for the set of parameter values that best describes the measured target. In order to assist the search, the calculations in step 306 may further generate partial derivatives of the merit function, indicating the sensitivity with which increasing or decreasing a parameter will increase or decrease the merit function, in this particular region in the parameter space. The calculation of merit functions and the use of derivatives is generally known in the art, and will not be described here in detail.

314: When the merit function indicates that this iterative process has converged on a solution with a desired accuracy, the currently estimated parameters are reported as the measurement of the actual target structure.

The steps of the above process have been presented in a certain order for the sake of explanation. They do not have to be performed in the order described. For example, steps 302 and/or 303 can be performed after making a measurement in step 304. The computation time of this iterative process is largely determined by the forward diffraction model used, i.e. the calculation of the estimated model diffraction pattern using a rigorous optical diffraction theory from the estimated target structure. If more floating parameters are required, then there are more degrees of freedom. The calculation time increases with the number of degrees of freedom. The estimated or model diffraction pattern calculated at 306 can be expressed in various forms. For example, a modeled diffraction spectrum can be compared easily with a diffraction spectrum measured by the scatterometer apparatus of FIG. 2, when the model includes the optical behavior of the apparatus, from illumination source 11 to detector 19, as well as the scattering behavior of the target under inspection. This becomes an important consideration when many targets are to be measured on every substrate.

Throughout this description from FIG. 3 onward, the term 'diffraction pattern' will be used as an example of a detected signal on the assumption that an angularly resolved scatterometer is used, as described in the example apparatus of FIG. 2 and in the prior publication US 2012/0123748A1, mentioned above. The skilled person can readily adapt the teaching to different types of scatterometer, to ellipsometers, optical profile measurement systems, or even other types of measurement instrument and to diffraction patterns which are spectrally resolved, for example.

In summary, the process of FIG. 3 uses a model fit approach to infer parameters of a target structure from a scatterometry measurement signal. The floating parameters may be relevant only internally of the model, or may be genuine parameters of interest which the system user wants to determine through the measurement and reconstruction process. While the concept is simple in principle, in practice it is difficult to design the reconstruction model. The model should be optimized for accuracy, which may be defined for example by root mean square error (RMSE), and may be decomposed into noise sensitivity (reproducibility) and bias (systematic error). The model optimization should also achieve an optimal measurement response to actual variations of the parameters of interest, while being insensitive to the influence of noise, calibration errors, model approximations and variation of other parameters. Finally, the model runtime should be minimized.

The above techniques can also be used to make CD (or other) measurements robust to measurement context variations including spot positioning, focus, metrology tool (matching), measurement radiation and reproducibility due to wafer load/unload. The techniques described can also be used for other measurements using model fits, e.g. overlay measurements. The techniques can also be applicable to other metrology tools and measurements such as through-wavelength measurements performed with an alignment sensor of a lithographic apparatus.

Although patterning devices in the form of a physical reticle have been described, the term "patterning device" in this application also includes a data product conveying a pattern in digital form, for example to be used in conjunction with a programmable patterning device.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the present invention are further described in below numbered clauses:

1. A method of measuring a parameter of interest relating to a structure on a substrate, comprising:
   1) determining a correction to compensate for the effect of a measurement condition on a measurement signal from a plurality of measurement signals, wherein each of said measurement signals results from a different measurement of the structure performed under a different variation of said measurement condition; and
   2) performing a reconstruction of a mathematical model of said structure using the correction to suppress an influence of variations of said measurement condition on the reconstruction.

2. A method according to clause 1, further comprising: 3) reporting a measurement of said parameter of interest based on the reconstruction.

3. A method according to clause 1 or 2, wherein the step of performing a reconstruction of a mathematical model of said structure comprises:
   a) defining a mathematical model in which shape and material properties of said structure, are represented by a plurality of parameters including at least one parameter of interest;
   b) calculating a model signal using said mathematical model;
   c) determining a degree of matching between a measurement signal resulting from a measurement of the structure and the model signal, while using the correction to suppress the influence of variations of said measurement condition which are not sufficiently represented in the model signal on the degree of matching; and
   d) determining a set of parameter values for said plurality of parameters that provides a sufficiently high degree of matching.

4. A method according to clause 3, wherein said steps b) to d) are performed iteratively while varying the value of one or more of said plurality of parameters to minimize a difference between the measurement signal and the model signal while applying the correction at each iteration of the minimization.

5. A method according to clause 4, wherein steps c) and d) comprise performing a direct inversion to minimize a misfit between the measurement signal and the model signal to determine the set of parameter values.

6. A method according to clause 4, wherein step b) is performed in advance for a plurality of different sets of parameter values so as to calculate a library of candidate model signals and steps c) and d) comprise determining a degree of matching between the measurement signal and said candidate model signals until said degree of matching is sufficiently high.

7. A method according to any of clauses 3 to 6, wherein said correction comprises a weighting function or weighting matrix operable such that the degree of matching between the detected signal and a model signal determined at step c) has a dependence on different components of the signals defined by the weighting function or weighting matrix.

8. A method according to clause 7, wherein step c) comprises applying the weighting function or weighting matrix to a difference between the measured signal and model signal.

9. A method according to clause 7 or 8, wherein said detected signal is a two-dimensional diffraction pattern obtained by angle-resolved scatterometry, and said weighting function or weighting matrix defines for some components in said diffraction pattern a lower weight than other components for calculating the degree of matching.

10. A method according to clause 7 or 8, wherein said detected signal is a two-dimensional spectral resolved diffraction pattern obtained by reflectometry or ellipsometry, and said weighting function or weighting matrix defines for some components in said diffraction pattern a lower weight than other components for calculating the degree of matching.

11. A method according to clause 9 or 10, wherein said weighting function or weighting matrix comprises a matrix describing the per-component variance of the plurality of measurement signals, and which imposes a lesser weighting to components which show the greatest variance over the plurality of measurement signals.

12. A method according to clause 9 or 10, wherein said weighting function or weighting matrix comprises a matrix describing the per-component variance of the plurality of measurement signals and covariance between each pair of the plurality of measurement signal components; and which imposes in general a lesser weighting to components which show the greatest variance and/or pairs of components which show the greatest magnitude covariance over the plurality of measurement signals.

13. A method according to any of clauses 7 to 12, wherein the weighting function or weighting matrix is combined with a detector noise weighting function or weighting matrix which compensates for noise on a detector used to detect the measurement signals.

14. A method according to any of clauses 7 to 13, comprising:
performing steps 1) to 2) for a plurality of different measurement conditions to obtain a plurality of measurement condition varied weighting matrices, each relating to a different one of said measurement conditions; and
combining said plurality of measurement condition varied weighting matrices to obtain said weighting function or weighting matrix.

15. A method according to any of clauses 7 to 14, comprising:
performing steps 1) to 2) for a plurality of different but equivalent structures to obtain a plurality of structure varied weighting matrices, each relating to a different one of said structures;
averaging said plurality of structure varied weighting matrices to obtain said weighting function or weighting matrix.

16. A method according to any preceding clause, wherein the measurements performed under different variations of a measurement condition comprise measurements performed with a measurement parameter varied.

17. A method according to clause 16, wherein the measurement parameter comprises position of a measurement spot in the plane of the substrate with respect to the structure.

18. A method according to clause 16, wherein the measurement parameter comprises focus of a measurement spot on the structure.

19. A method according to clause 16, wherein the measurement parameter comprises a parameter of measurement radiation used to perform the measurements.

20. A method according to clause 19, wherein the measurement parameter is the wavelength or wavelengths of the measurement radiation.

21. A method according to clause 19, wherein the measurement parameter is the bandwidth of the measurement radiation.

22. A method according to clause 19, wherein the measurement parameter is the angle of incidence of a measurement beam.

23. A method according to any of clauses 1 to 15, wherein the measurements performed under different variations of a measurement condition comprise measurements performed on different metrology apparatuses.

24. A method according to any of clauses 1 to 15, wherein the measurements performed under different variations of a measurement condition comprise measurements performed before and after an unloading and reloading step, during which the substrate is unloaded and reloaded.

25. A method according to any preceding clause, wherein the correction comprises a weighting factor which imposes a weighting on each measurement signal from the plurality of measurement signals during the step of determining a correction, the weighting being based on the relative likelihood of the particular variation of the measurement condition which corresponds to that measurement signal.

26. A method according to any preceding clause, wherein the parameter of interest is a physical dimension of said structure.

27. A method according to any of clauses 1 to 25, wherein the parameter of interest is overlay.

28. A metrology apparatus arranged to perform the method of any of clauses 1 to 27.

29. A metrology apparatus, comprising:
a support for a substrate on which a structure is formed;
an optical system for selectively illuminating said structure with radiation and collecting at scattered radiation which has been scattered by the structure, for a plurality of different variations of a measurement condition;
a detector for detecting a measurement signal from the scattered radiation, for each variation of a measurement condition; and
a processor arranged to determine a correction to compensate for the effect of the measurement condition on a measurement signal from the measurement signals detected.

30. A metrology apparatus according to clause 29, wherein said processor is further operable to perform a reconstruction of a mathematical model of said structure using the correction to suppress an influence of variations of said measurement condition on the reconstruction; and to report a measurement of a parameter of interest of said structure based on the reconstruction.

31. A metrology apparatus according to clause 30, wherein the parameter of interest is a physical dimension of said structure.

32. A metrology apparatus according to clause 30, wherein the parameter of interest is overlay.

33. A metrology apparatus according to any of clauses 30 to 32, wherein said processor is further operable to:
a) define a mathematical model in which shape and material properties of said structure, are represented by a plurality of parameters including at least one parameter of interest;
b) calculate a model signal using said mathematical model;
c) determine a degree of matching between a measurement signal resulting from a measurement of the structure and the model signal, while using the correction to suppress the influence of variations of said measurement condition which are not sufficiently represented in the model signal on the degree of matching; and d) determine a set of parameter values for said plurality of parameters that provides a sufficiently high degree of matching.

34. A metrology apparatus according to clause 33, being operable to calculate a model signal and determine a degree of matching iteratively while varying the value of one or more of said plurality of parameters to minimize a difference between the measurement signal and the model signal while applying the correction at each iteration of the minimization.

35. A metrology apparatus according to clause 33, being operable to perform a direct inversion to minimize a misfit between the measurement signal and the model signal to determine the set of parameter values.

36. A metrology apparatus according to clause 33, being operable to obtain a library of candidate model signals and determine a degree of matching between the measurement signal and said candidate model signals until said degree of matching is sufficiently high.

37. A metrology apparatus according to any of clauses 33 to 36, wherein said correction comprises a weighting function or weighting matrix operable such that the degree of matching between the detected signal and a model signal has a dependence on different components of the signals defined by the weighting function or weighting matrix.

38. A metrology apparatus according to clause 37, operable to apply the weighting function or weighting matrix to a difference between the measured signal and model signal.

39. A metrology apparatus according to clause 37 or 38, wherein said detected signal is a two-dimensional diffraction pattern obtained by angle-resolved scatterometry, and said weighting function or weighting matrix defines for some components in said diffraction pattern a lower weight than other components for calculating the degree of matching.

40. A metrology apparatus according to clause 37 or 38, wherein said detected signal is a two-dimensional spectral resolved diffraction pattern obtained by reflectometry or ellipsometry, and said weighting function or weighting matrix defines for some components in said diffraction pattern a lower weight than other components for calculating the degree of matching.

41. A metrology apparatus according to clause 39 or 40, wherein said weighting function or weighting matrix comprises a variance matrix describing the per-component variance of the plurality of measurement signals, and which imposes a lesser weighting to components which show the greatest variance over the plurality of measurement signals.

42. A metrology apparatus according to clause 39 or 40, wherein said weighting function or weighting matrix comprises a covariance matrix describing the per-component variance of the plurality of measurement signals and covariance between each pair of the plurality of measurement signals; and which imposes a lesser weighting to components which show the greatest variance and/or pairs of components which show the greatest magnitude covariance over the plurality of measurement signals.

43. A metrology apparatus according to any of clauses 37 to 42, being operable to combine the weighting function or weighting matrix with a detector noise weighting function or weighting matrix which compensates for noise on a detector used to detect the measurement signals.

44. A metrology apparatus according to any of clauses 37 to 43, operable to determine a plurality of measurement condition varied weighting matrices, each relating to a different measurement condition; and combine said plurality of measurement condition varied weighting matrices to obtain said weighting function or weighting matrix.

45. A metrology apparatus according to any of clauses 37 to 44, operable to determine a plurality of structure varied weighting matrices, each relating to a different but equivalent structure; and average said plurality of structure varied weighting matrices to obtain said weighting function or weighting matrix.

46. A metrology apparatus according to any of clauses 29 to 45, wherein the different variations of a measurement condition comprise the variation of a measurement parameter.

47. A metrology apparatus according to clause 46, wherein the measurement parameter comprises a position of a measurement spot in the plane of the substrate with respect to the structure, defined when selectively illuminating said structure with radiation.

48. A metrology apparatus according to clause 46, wherein the measurement parameter comprises focus of a measurement spot defined when selectively illuminating said structure with radiation on the structure.

49. A metrology apparatus according to clause 46, wherein the measurement parameter comprises a parameter of the radiation used to selectively illuminate said structure.

50. A metrology apparatus according to clause 49, wherein the measurement parameter is the wavelength or wavelengths of the radiation.

51. A metrology apparatus according to clause 49, wherein the measurement parameter is the angle of incidence of a measurement beam of the radiation used to selectively illuminate said structure.

52. A metrology apparatus according to clause 49, wherein the measurement parameter is the bandwidth of the measurement radiation.

53. A metrology apparatus according to any of clauses 29 to 45, wherein the different variations of a measurement condition comprise conditions before and after an unloading and reloading step, during which the substrate is unloaded and reloaded.

54. A metrology apparatus according to any of clauses 29 to 53, wherein the correction comprises a weighting factor which imposes a weighting on each measurement signal during the step of determining a correction, the weighting being based on the relative likelihood of the particular variation of the measurement condition which corresponds to that measurement signal.

55. A lithographic system comprising:

a lithographic apparatus for use in a lithographic process; and a metrology apparatus according to any of clauses 28 to 54.

56. A computer program product comprising machine readable instructions which, when run on a suitable processor, cause the processor to perform the method of any of clauses 1 to 27.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of metrology in a metrology apparatus for measuring a parameter of interest relating to a structure, the structure formed using a lithographic process of a lithographic system on a substrate, comprising:
   receiving, from an optical detector of the metrology apparatus, a plurality of measurement signals representing scattered radiation of a plurality of different variations of a measurement condition of the metrology apparatus to measure the structure, wherein each of the plurality of measurement signals results from a different measurement of the structure performed under a different variation of the measurement condition;
   determining, by a hardware processor, a correction to compensate for an effect of the measurement condition based on the plurality of measurement signal
   performing, by the hardware processor, a reconstruction of a mathematical model of the structure using the correction to reduce a merit function indicating an influence of variations of the measurement condition based on the reconstruction; and
   repeating, by the hardware processor, the determining and performing until the merit function converges on a solution with a preset accuracy.

2. The method of claim 1, further comprising:
   outputting a measurement of the parameter of interest based on the reconstruction when the merit function converges on the solution with the preset accuracy.

3. The method of claim 1, wherein the performing a reconstruction of the mathematical model of the structure comprises:
   defining a mathematical model in which shape and material properties of the structure are represented by a plurality of parameters including at least one parameter of interest;
   calculating a model signal using the mathematical model;
   determining a degree of matching between a measurement signal resulting from a measurement of the structure and the model signal, while using the correction to suppress the influence of variations of the measurement condition which are not sufficiently represented in the model signal on the degree of matching; and
   determining a set of parameter values for the plurality of parameters that provides a sufficiently high degree of matching.

4. The method of claim 3, wherein the correction comprises a weighting function or weighting matrix operable such that the degree of matching between the detected signal and a model signal has a dependence on different components of the detected and model signals defined by the weighting function or weighting matrix.

5. The method of claim 1, wherein the measurements performed under different variations of the measurement condition comprise measurements performed with a measurement parameter varied.

6. The method of claim 1, wherein the measurements performed under different variations of the measurement condition comprise measurements performed on different metrology apparatuses.

7. The method of claim 1, wherein the measurements performed under different variations of the measurement condition comprise measurements performed before and after an unloading and reloading of the substrate.

8. The method of claim 1, wherein the correction comprises a weighting factor which imposes a weighting on each measurement signal from the plurality of measurement signals during the determining a correction, the weighting being based on a relative likelihood of a particular variation of the measurement condition which corresponds to that measurement signal.

9. A metrology apparatus, comprising:
   a support configured to support a substrate on which a structure is formed;
   an optical system configured to selectively illuminate the structure with radiation and collect radiation scattered by the structure for a plurality of different variations of a measurement condition;
   a detector configured to detect a measurement signal from the scattered radiation for each variation of the plurality of variations of the measurement condition; and
   a processor arranged to:
      determine a correction to compensate for an effect of the measurement condition on a measurement signal from the measurement signal,
      perform a reconstruction of a mathematical model of the structure using the correction to reduce a merit function indicating an influence of variations of the measurement condition on the reconstruction, and
      repeat the determine a correction and the reconstruction until the merit function converges on a solution with a preset accuracy.

10. The metrology apparatus of claim 9, wherein the processor is further operable to:
   output a measurement of a parameter of interest of the structure based on the reconstruction when the merit function converges on the solution with the preset accuracy.

11. The metrology apparatus of claim 10, wherein the processor is further operable to:
   define a mathematical model in which shape and material properties of the structure, are represented by a plurality of parameters including at least one parameter of interest;
   calculate a model signal using the mathematical model;
   determine a degree of matching between a measurement signal resulting from a measurement of the structure and the model signal, while using the correction to suppress the influence of each variation of the plurality of variations of the measurement condition which are not sufficiently represented in the model signal based on the degree of matching; and
   determine a set of parameter values for the plurality of parameters that provides a sufficiently high degree of matching.

12. The metrology apparatus of claim 11, wherein the correction comprises a weighting function or weighting matrix operable such that the degree of matching between the detected signal and the model signal has a dependence on different components of the signals defined by the weighting function or weighting matrix.

13. The metrology apparatus of claim 9, wherein the plurality of different variations of the measurement condition comprise the variation of a measurement parameter.

14. The metrology apparatus of claim 9, wherein the plurality of different variations of the measurement condition comprise conditions before and after an unloading and reloading of the substrate.

15. The metrology apparatus of claim 9, wherein the correction comprises a weighting factor which imposes a weighting on each measurement signal during the determining a correction, the weighting being based on a relative likelihood of a particular one of the plurality of different variations of the measurement condition which corresponds to that measurement signal.

16. A lithographic system comprising:
   a lithographic apparatus for use in a lithographic process; and
   a metrology apparatus comprising:
      a support configured to support a substrate on which a structure is formed;
      an optical system configured to selectively illuminate the structure with radiation and collect radiation scattered by the structure for a plurality of different variations of a measurement condition;
      a detector configured to detect a measurement signal from the scattered radiation for each variation of the plurality of variations of the measurement condition; and
      a processor arranged to:
         determine a correction to compensate for an effect of the measurement condition on a measurement signal from the measurement signal,
         perform a reconstruction of a mathematical model of the structure using the correction to reduce a merit function indicating an influence of variations of the measurement condition on the reconstruction, and
         repeat determining the correction and performing the reconstruction until the merit function converges on a solution with a preset accuracy.

17. A non-transitory computer program product comprising machine readable instructions which, when run on a suitable processor, cause the processor to perform a method of metrology in a metrology apparatus for measuring a parameter of interest relating to a structure, the structure formed using a lithographic process of the lithographic system on a substrate, the method comprising:
   receiving, from an optical detector of the metrology apparatus, a plurality of measurement signals representing scattered radiation of a plurality of different variations of a measurement condition of the metrology apparatus to measure the structure, wherein each of the plurality of measurement signals results from a different measurement of the structure performed under a different variation of the measurement condition;
   determining a correction to compensate for an effect of the measurement condition based on the plurality of measurement signals;
   performing a reconstruction of a mathematical model of the structure using the correction to reduce a merit function indicating an influence of variations of the measurement condition on the reconstruction; and
   repeating the determining and performing until the merit function converges on a solution with a preset accuracy.

\* \* \* \* \*